US005137809A

United States Patent [19]
Loken et al.

[11] Patent Number: 5,137,809
[45] Date of Patent: Aug. 11, 1992

[54] METHOD TO DETERMINE THE COMPOSITION OF BONE MARROW SAMPLES

[75] Inventors: Michael R. Loken, Los Altos, Calif.; Curt I. Civin, Baltimore, Md.; Virendra O. Shah, Cupertino, Calif.

[73] Assignee: Becton, Dickinson and Company, Franklin Lakes, N.J.

[21] Appl. No.: 572,303

[22] Filed: Jul. 19, 1990

Related U.S. Application Data

[63] Continuation of Ser. No. 118,498, Nov. 9, 1987, abandoned.

[51] Int. Cl.$^5$ .......................................... G01N 33/533
[52] U.S. Cl. ................................... 435/7.21; 435/7.1; 435/7.2; 422/61; 436/800; 436/546
[58] Field of Search ................. 435/4, 7.24, 29, 7.1, 435/7.2, 7.21; 436/546

[56] References Cited

U.S. PATENT DOCUMENTS

| | | | |
|---|---|---|---|
| 4,581,334 | 4/1986 | Kirchanski et al. | 435/29 |
| 4,599,301 | 7/1986 | Lanier et al. | 435/7 |
| 4,599,304 | 7/1986 | Lanier et al. | 935/108 X |
| 4,645,738 | 2/1987 | Knowles et al. | 436/519 X |
| 4,654,312 | 3/1987 | Chang et al. | 436/519 |
| 4,727,020 | 2/1988 | Recktenwald | 435/6 |

FOREIGN PATENT DOCUMENTS 0219309  4/1987  European Pat. Off. .

OTHER PUBLICATIONS

Lanier et al., "Human Lymphocyte Seebpopulations Identified by Using Three-Color Immunofluorescence . . . ", J. Immunol. 132(1), 151–6 (1984).
Horan et al., "Improved Flow Cytometric Analysis of Leukocyte Subsets . . . ", PNAS 83, 8361–8365 (Nov. 1986).
Hoffman et al., "Simple and Rapid Measurement of Human T Lymphocytes and Their Subclasses . . . ", PNAS 77, 4914–4917 (Aug. 1980).
Rabinovitch et al., "Sumultaneous Cell Cycle Analysis and Two–Color Surface Immunofluorescence . . . ", J. Immunol. 136(8), 2769–2775 (Apr. 18, 1986).
Loken et al., Blood, 69:255–263 (1987).
Civin et al., Exp. Hematol., 15:10–17 (1987).
Loken, Monoclonal Antibodies, Church. II Livingstone (P. Beverley ed.) (1986).
Loken et al., Blood, 70:1316–1324 (1987).
Strauss et al., Exp. Hematol., 14:935–945 (1986).

Primary Examiner—Christine Nucker
Assistant Examiner—Jeffrey Stucker
Attorney, Agent, or Firm—Robert M. Hallenbeck

[57] ABSTRACT

A method and kit for identification of the lineages and stages of hematopoietic cells in a sample wherein the cells are treated with labeled monoclonal antibodies selected to distinguish between each lineage and maturational stages within each lineage.

14 Claims, 10 Drawing Sheets

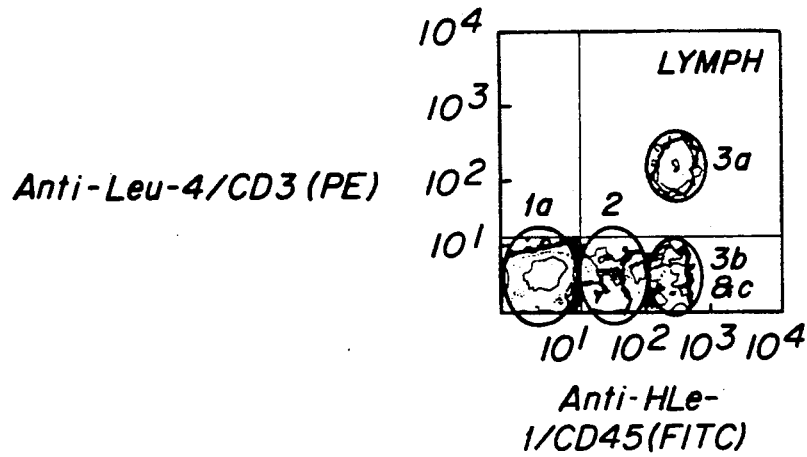
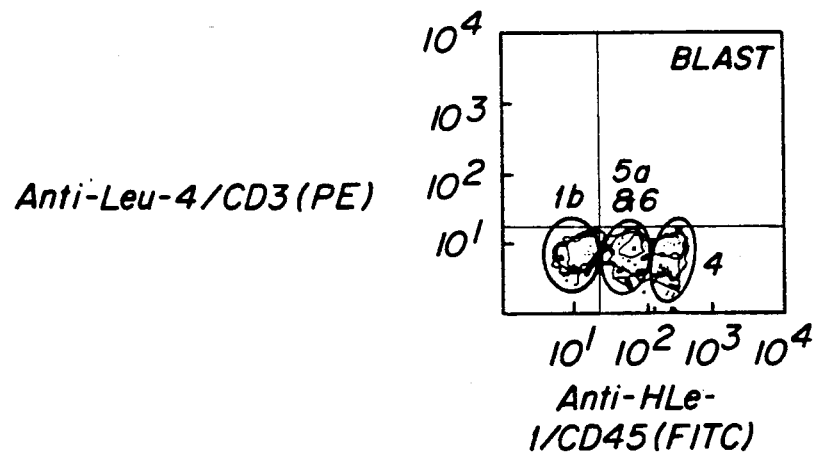
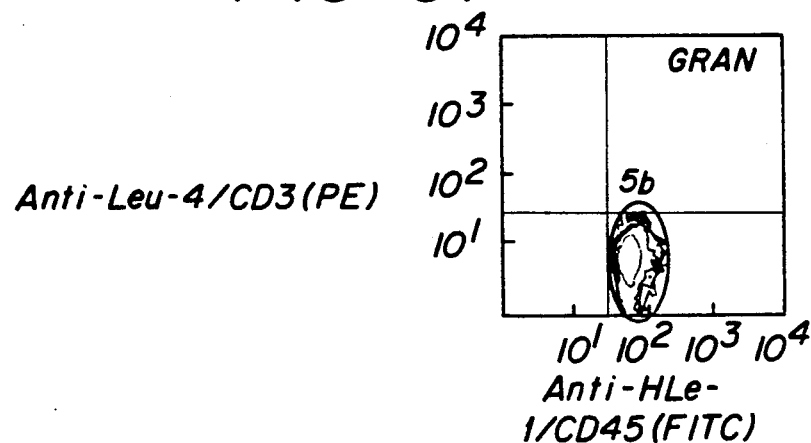

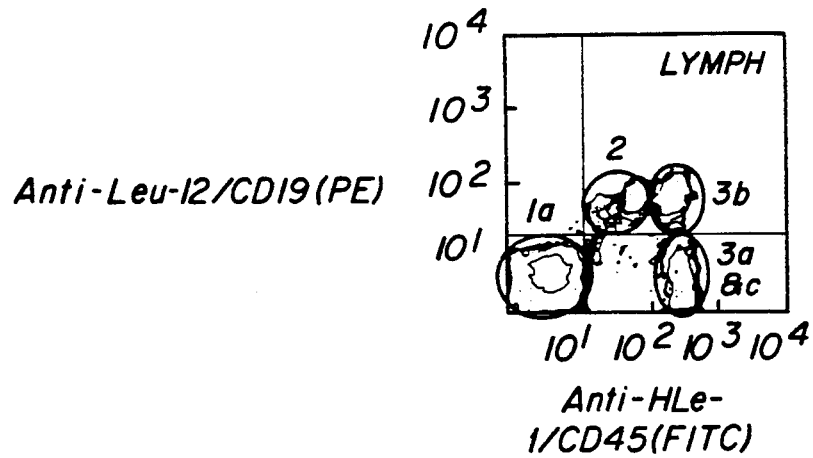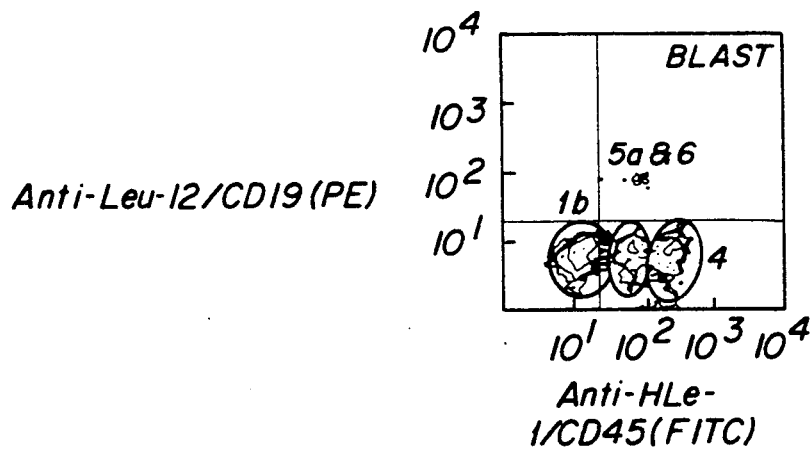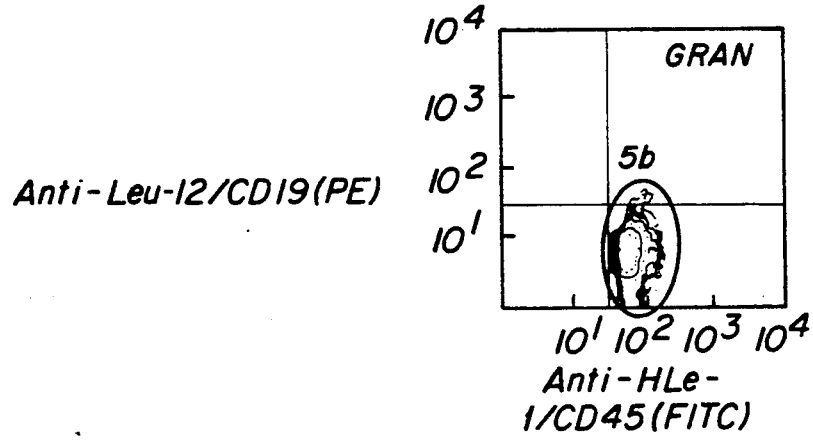

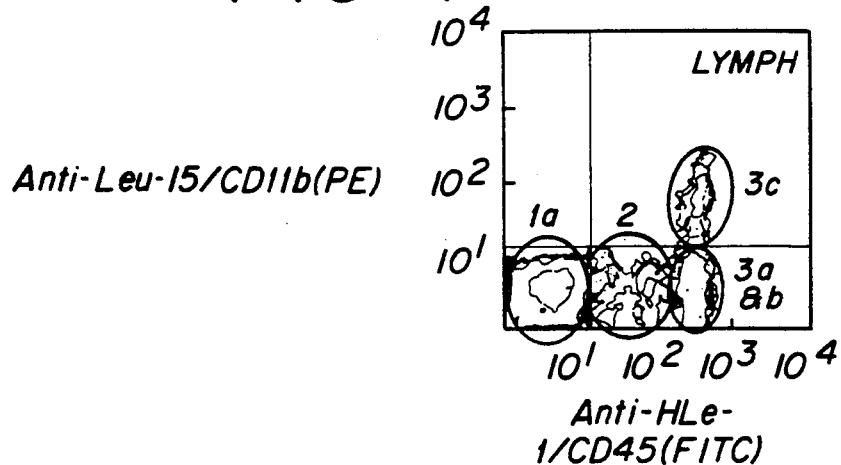
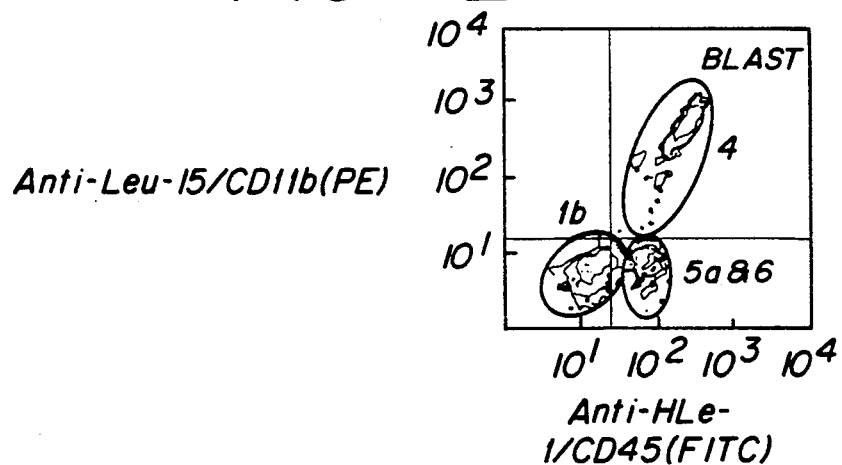
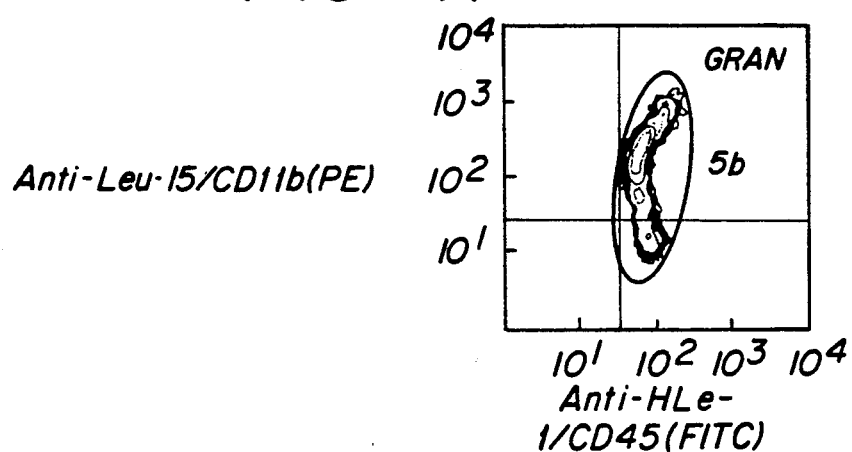

METHOD TO DETERMINE THE COMPOSITION OF BONE MARROW SAMPLES

This application is a continuation of application Ser. No. 118,498, filed Nov. 9, 1987, now abandoned.

FIELD OF THE INVENTION

The present invention relates to the detection and analysis of hematopoietic cells in a sample, and more particularly relates to a method for the detection and analysis of immature and mature cells of different lineages in a bone marrow sample using labeled monoclonal antibodies and the light scattering properties of the cells.

BACKGROUND OF THE INVENTION

Bone marrow is a complex tissue. Principally, marrow is the site for the differentiation and maturation of hematopoietic cells. From pluripotent stem cells, a number of cell lineages differentiate. The primary components among these lineages include: the lymphoid (B, T and NK cells), the erythroid (red blood cells) and the myeloid lines (basophils, neutrophils, eosinophils, megakaryocytes and macrophages). At any given time, each of these lineages typically is present in a marrow sample.

Once differentiated, each of the various lineages matures through several stages. Maturation occurs in the marrow and elsewhere. For example, in the erythroid line, the red blood cell begins in marrow as a blast cell having a defined morphology. From that stage to the reticulocyte stage, a number of additional morphological changes occur throughout a number of stages culminating with the extrusion of the nucleus to form the reticulocyte. The reticulocyte then is released to the blood where it undergoes its final maturational change to become an erythrocyte. Other lineages undergo similar development, although the number of stages of development and the location may differ (e.g. immature T cells begin to develop in marrow but the primary location for maturation and differentiation is in the thymus). By examining a sample of bone marrow, therefore, one can identify not only the various lineages within the sample but also the several stages within each lineage.

It is important to be able to identify the lineages and/or developmental stages in a sample. The results may provide an indication of a clinical condition. For example, in a patient with anemia, in order to treat the cause of the condition one must know whether it is the result of a destruction of red cells in the blood or the result of a failure of the blast cells to mature. By examining the marrow, the presence (or absence) of stem cells, blasts and reticulocytes in normal amounts can rule out (or confirm) a diagnosis. Thus, by distinguishing a change from the "normal" condition, abnormal events can be diagnosed.

To identify the various lineages and developmental stages, one must examine a sample in great detail. It is known that each lineage and each stage within a lineage has certain defined morphological characteristics. Thus, the current practice is to take a sample of marrow by either aspiration or biopsy, stain it and examine it under a light microscope. Such a procedure is subjective, time-intensive, semi-quantitative and may require multiple stainings in order to obtain gross results.

In addition to gross morphological changes that occur with maturation and differentiation, other detailed changes occur in gene expression. A number of studies have described the appearance (or disappearance) during maturation of a variety of such cell surface antigens in a single lineage (e.g., normal erythrocytes) and for a single antigen expressed on several lineages during their maturational process. See, e.g., Loken et al., Flow Cytometric Analysis of Human Bone Marrow: I. Normal Erythroid Development, Blood, 69:255-263 (1987), and see Civin et al., Antigenic Analysis of Hematopoiesis. VI. Flow Cytometric Characterization of MY-10-positive Progenitor Cells in Normal Human Bone Marrow, Exp. Hematol., 15:10-17 (1987) respectively. Because of the cellular heterogeneity of cells within marrow, the use of markers to detect cell surface antigens was not fully sufficient to distinguish between lineages.

Thus, there was no known means to identify and distinguish between lineages and stages of development in single procedure. Such a method would provide a unique and rapid technique for the diagnosis of abnormal hematopoietic conditions.

BRIEF DESCRIPTION OF THE INVENTION

The present invention is directed to a method and kit for the identification and analysis of lineages and maturational stages in normal hematopoietic cells. In accordance with one embodiment of the invention, a sample of bone marrow is taken from an individual. The sample is treated to provide a second sample comprising essentially only leukocytes. A first monoclonal antibody is labeled with a first fluorochrome. The first monoclonal antibody is selected so that it reacts with substantially all leukocytes. A second monoclonal antibody is labeled with a second fluorochrome. The second monoclonal antibody is selected so that it reacts with a subpopulation of leukocytes (e.g., monocytes and granulocytes). The first fluorochrome and second fluorochrome are selected so that each has a similar excitation energy level but have distinct emission spectra.

A mixture of the second sample, first fluorochrome labeled monoclonal antibody and second fluorochrome labeled monoclonal antibody then is prepared so as to cause the leukocytes in the mixture to become labeled with the first monoclonal antibody and the subpopulation of leukocytes to become labeled with the second monoclonal antibody. The mixture then is analyzed by flow cytometry so as to distinguish lineages by cell size and granularity, and at the same time, the distribution of the binding of the first and second antibodies on the cells is recorded. The combination of all four parameters provides data sufficient to distinguish between each lineage and stages within each lineage. The data may be stored in a data collection means, such as a computer.

Figure 1:
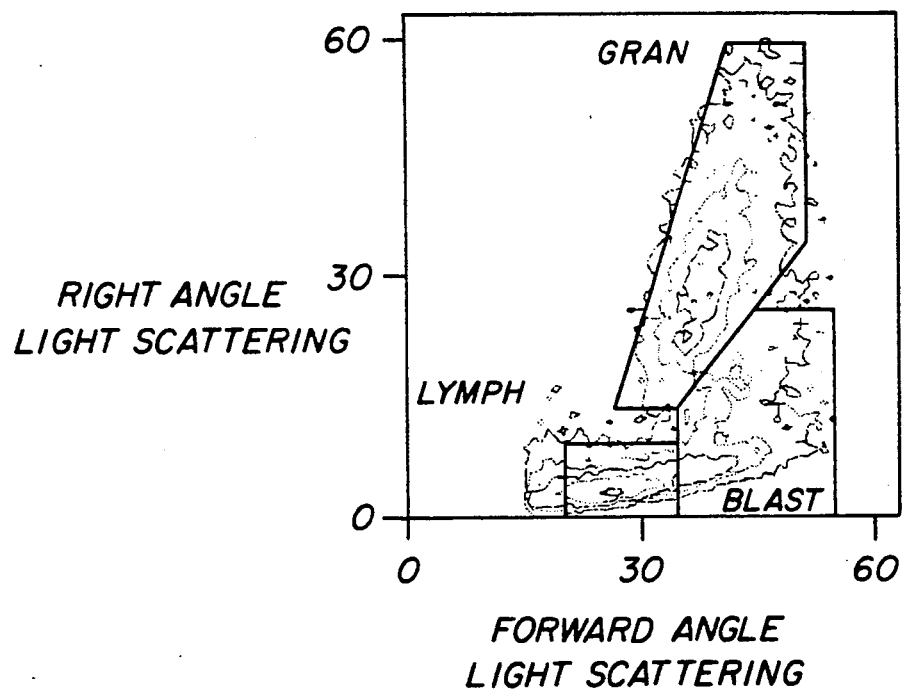
FIG. 1 is a contour plot of forward light scatter versus side (or "right angle") light scatter for a sample of normal human bone marrow analyzed by flow cytometry.

as analyzed by flow cytometry with gates set to exclude all cells but those that appear in the "LYMPH", "BLAST" or "GRAN" window of FIG. 1.

DETAILED DESCRIPTION OF THE INVENTION

Bone marrow aspirates were obtained from normal adults. Although bone marrow was the source of hematopoietic cells in the following examples, it should be apparent to those skilled in the art that hematopoietic cells also may be isolated from the blood. It is not necessary to alter the method of invention to identify cells from this source.

Low density leucocytes (obtained by density gradient centrifugation using 1.077 g/cm$^3$, Ficoll-Hypaque, Pharmacia, Piscataway, N.J.) were washed in RPMI 1640 (GIBCO) containing 10% fetal bovine serum and aliquoted for immunofluorescent staining. Low-density leukocytes were used to form the first sample. It should be apparent to those skilled in the art, however, that whole blood or marrow aspirates may be used. In such causes, ammonium chloride, for example, may be used to prepare the first sample.

Low density marrow leukocytes were suspended at a concentration of 10$^7$ per ml. In those experiments where both antibodies were directly conjugated to the fluorochrome, the first antibody was added to 10$^6$ cells using an amount of antibody which gave maximal fluorescence. The cells were incubated on ice for 20 minutes. The cells were then pelleted and washed with RPMI 1640 buffer (at least 5 times the staining volume) before adding the second antibody. After 20 minutes on ice, the cells were again washed with buffer, then fixed in 1% paraformaldehyde.

In experiments where only one directly fluorochrome conjugated antibody was available, a four step procedure was used. The cells were first reacted with unconjugated antibody. Following the wash step, the cells were reacted with rat anti-mouse Kappa (PE), incubated on ice, and washed. The cells were then exposed to 10% normal mouse serum to block free binding sites of the second-step antibody. The cells were then stained with the second (directly conjugated) monoclonal antibody, washed and fixed as before.

For three-color analysis, cells were reacted first with unconjugated antibody followed by rat anti-mouse Kappa-APC second step antibody. Cells were washed, reacted with 10% normal mouse serum, followed by PE-conjugated and FITC-conjugated antibodies for 20 minutes, washed and fixed as before.

Fluorescein isothiocyanate (FITC) conjugated and/or phycoerythrin (PE) conjugated directly or indirectly CD3(Leu-4), CD10(CALLA), CD11b(Leu-15), CD14(Leu-M3), CD15(Leu-M1), CD19(Leu-12), CD20(Leu-16), CD45R(Leu-18), mouse IgG$_1$, mouse IgG$_2$, rat-anti-mouse Kappa, rat-anti-mouse Kappa-allophycocyanin (APC), and purified CD34(HPCA-1) were obtained from Becton Dickinson Immunocytometry Systems, Mountain View, Calif. Anti-glycophorin (10F7) was a kind gift from Dr. R. Langlois, Livermore, Calif.

Unstained cells, IgG$_1$-FITC, IgG$_2$-PE, and rat anti-mouse Kappa-APC labeled cells were included as controls.

Initially, bone marrow aspirates, prepared as above, were analyzed by flow cytometry. Presently known and available, flow cytometers are useful for measuring cell volume, forward light scatter and/or side light scatter. These parameters can then be used to separate lineages based upon their optical or physical characteristics.

Briefly, forward light scatter (FLS) provides a measurement of cell size. (Cell volume similarly measures cell size and an instrument so equipped may be used alternatively.) Side light scatter (SLS), on the other hand, approximates the "granularity" of the cell. SLS measures light reflected from the cell and is a function of the presence (or absence) of structures in the cell such as the nucleus and/or granules. Taken together, FLS and SLS can be used to aid in distinguishing between cells of different types.

In addition to FLS and SLS, flow cytometers include one or more, usually two, fluorescent channels. These channels are used to distinguish cells marked with fluorochromes which can be excited to emit light at different wave lengths. Separate antibodies labeled with distinct fluorochromes may be used to distinguish between cell types based on their expression of different cell surface antigens. By combining all four parameters together (i.e., FLS, SLS, FL1 and FL2), the lineages and their stages can be distinguished in four dimensional space.

Flow cytometric analyses were performed using a FACStar ™ for two color immunofluorescence and FACS 440 ™ for three color immunofluorescence (Becton Dickinson Immunocytometry Systems, Mountain View, Calif.). The argon ion laser was operated at 488nm using 200 mW of power. FITC emission was collected with a 530/30 BP filter, while PE emission was collected through a 585/42 BP filter. Three-color immunofluorescence was performed using a HeNe laser of 633 nm, 40 mW, along with an argon laser as described above. APC emission was collected with a 660/20 BP filter. 50,000 events was collected in list mode on a Consort 30 Data Management System (Becton Dickinson). This permitted reanalysis of the data to demonstrate the correlation between the different colors of immunofluorescence for populations of cells identified by forward and right-angle light scattering. For all contour plots, the lowest level was 3 events with contours drawn at 4, 6, 8, 10, 16, 32, 64, 128.

For a more detailed description of the use and meaning of these parameters, see Loken, Cell Surface Antigen and Morphological Characterization of Leucocyte Populations by Flow Cytometry, in Monoclonal Antibodies, Churchill Livingstone (P. Beverley ed.), 1986. Although the following cell analyses were performed by flow cytometry, it should be apparent to one skilled in the art that fluorescent light microscopy may be used alternatively to determine cell size, granularity and fluorescence.

Referring to FIG. 1, it will be seen that three distinct populations of cells appear to be distinguished by the physical parameters of forward and right angle light scattering. These windows have been labeled "LYMPH", "BLAST" and "GRAN". The remaining material generally comprises debris (i.e., ruptured cells and cell or other fragments).

Although FIG. 1 (and indeed all the remaining figures) is shown in 2-dimensional space, it should be apparent that this is done solely for the purpose of presenting the description of the invention in viewable form. It is not the intent to limit the invention to 2-D space; in fact, in the preferred embodiment, the measurements (i.e., FLS. SLS, FL1 and FL2) are taken in 4-D space.

In order to identify the various lineages that comprise normal bone marrow, a first monoclonal antibody was selected that would identify substantially all leukocytes in the sample. CD45 is an antigen found on substantially all leukocytes. (The "CD" or cluster designation was defined by the International Workshops on Human Differentiation Antigens. The parallel "Leu" system was defined by researchers at Stanford University.) By selecting a monoclonal antibody for this antigen, leukocytes can be labeled. Anti-HLe-1 is one such monoclonal antibody. Another such antibody is LCA (Coulter Electronics, Inc.). Anti-HLe-1 is sold commercially both purified and bound to (FITC). If a pure anti-CD45 antibody is used, it may be conjugated to a fluorochrome (e.g., FITC or PE) by means known to those skilled in the art.

A second monoclonal antibody was selected to identify a subpopulation of leukocyte lineages. In the preferred embodiment, the second monoclonal antibody identifies two lineages of leukocytes: namely monocytes and granulocytes. These lineages are identified by the CD15 antigen. By selecting a monoclonal antibody for this antigen, these two lineages can be identified. Anti-Leu-M1 is one such anti-CD15 antibody, and another is My1.

While the preferred second monoclonal antibody is anti-CD15 and more specifically Anti-Leu-M1, it should be apparent to those skilled in the art from the Figures and following examples that other monoclonal antibodies may be used so long as they distinguish between the various lineages and maturational stages. For example, anti-CD11b, anti-CD16 and anti-CD19 (i.e., Anti-Leu-15, Anti-Leu-11 and Anti-Leu-12 respectively) all function to discriminate lineages and stages. Accordingly, these and other monoclonal antibodies referred to in the examples may be used in place of anti-CD15 (or Anti-Leu-M1).

Anti-Leu-M1 is commercially available in purified form but may be reacted with a second step (PE) conjugated antibody by means known to those skilled in the art in order to be paired with Anti-HLe-1(FITC). PE is chosen because it has a wavelength of excitation substantially similar to that of FITC but emits in a different spectrum. Once selected, the fluorochrome labeled first and second monoclonal antibodies can be combined with the sample as previously described. Anti-HLe-1(FITC) and Anti-Leu-M1(PE) are the preferred first and second monoclonal antibodies respectively.

Once the physical parameters of the cells in the sample are known as measured by FLS and SLS, gates may be established for each population in order to continue to view the invention in 2-D space. The gate will effectively exclude information from analysis for all cells outside the gate. When the gates are set for "LYMPH", "BLAST" and "GRAN" sequentially using Anti-HLe-1(FITC) and Anti-Leu-M1(PE), each lineage of cells is discernible as are the several stages of each lineage.

Figure 2A:
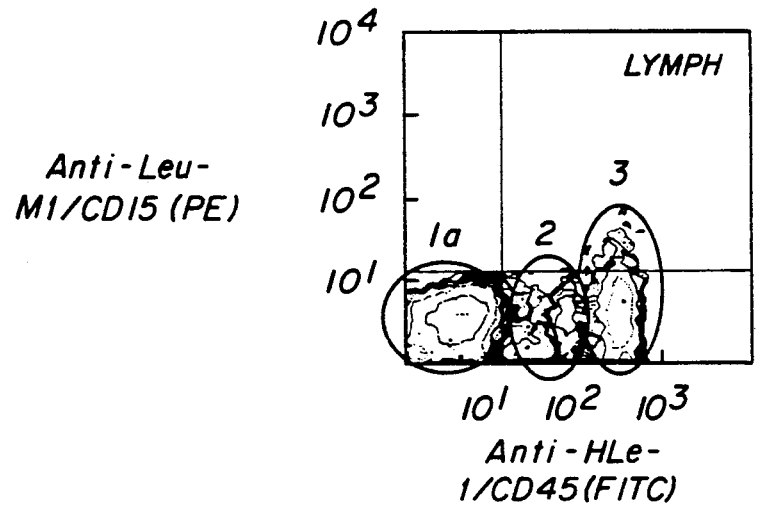
FIG. 2 is a contour plot of cells in normal human bone marrow labeled with Anti-Leu-M1(PE) and Anti-HLe-1(FITC) as analyzed by flow cytometry with gates set to exclude all cells but those that appear in the "LYMPH", "BLAST" or "GRAN" window of FIG. 1.
Figure 2B:
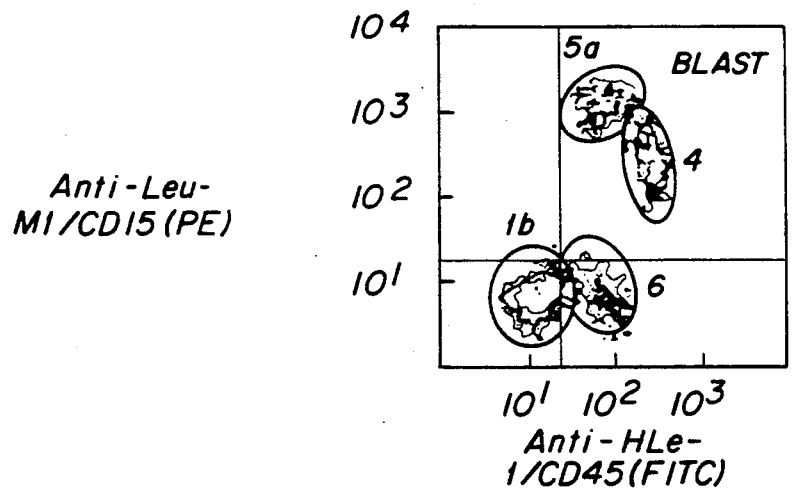
Figure 2C:
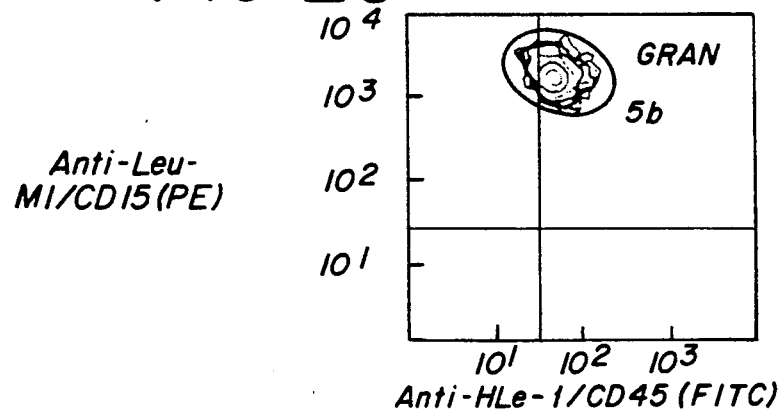

Referring to FIG. 2, the "LYMPH" window of bone marrow cells contains a mixture of lymphoid cells (population 2 pre-B cells, population 3 mature lymphoid cells) and mature erythrocytes (population 1a), along with nucleated erythroid precursor cells (population 1a). The "BLAST" window contains immature and mature monocytes (population 4), and immature cells of various blood cell lineages (population 1b early erythroid, 5a early neutrophils and population 6 blast cells). The "GRAN" window consists entirely of maturing granulocytes (population 5b). These results may be confirmed by light microscopic examination of the cells in accordance with standard staining procedures as described in Loken et al., supra.

To further confirm that the lineages identified in FIG. 2 were as described, a series of flow cytometry analyses were done with monoclonal antibodies specific for each lineage.

Figure 3A:
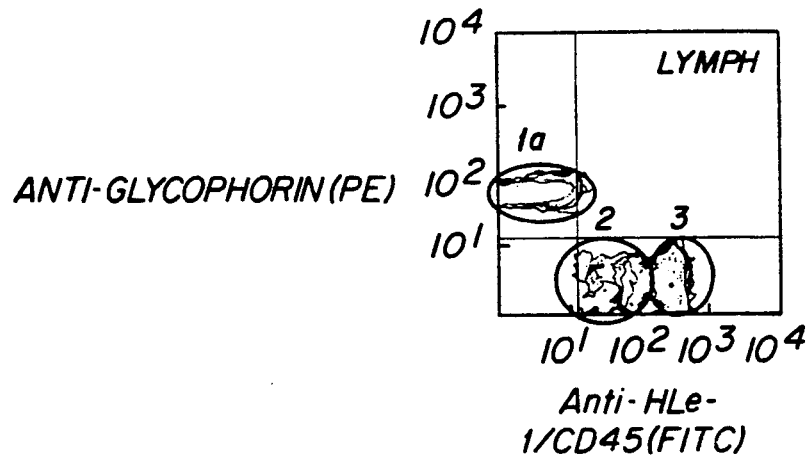
FIGS. 3-5 are contour plots of cells in normal human bone marrow labeled with various monoclonal antibodies coupled to PE and labeled with Anti-HLe-1(FITC)

To detect erythrocytes, human bone marrow cells were reacted with anti-glycophorin(PE), an antibody that identified erythroid cells, and with Anti-HLe-1(FITC). The correlation between these two markers, gated on forward and side light scattering, is shown in FIG. 3A. In the "LYMPH" window, GPA+/CD45− mature erythroid cells (population 1a) were easily distinguished from GPA−/CD45+ lymphoid cells (population 2,3). There were no GPA+ cells in the "GRAN" window.

In the "BLAST" window, distinct strongly GPA+ early erythroid cells (population 1b) were discriminated from cells expressing intermediate amount of GPA. See FIG. 3A. CD45 expression progressively decreased as cells became committed to the erythroid lineage, with increased expression of GPA.

Figure 3B:
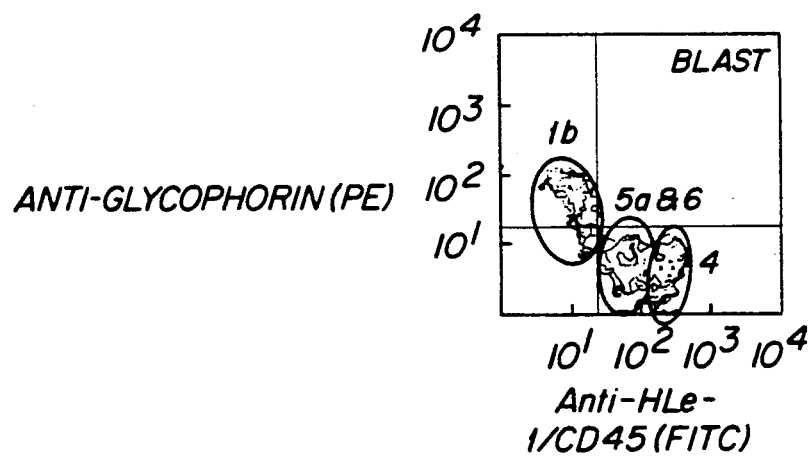
Figure 3C:
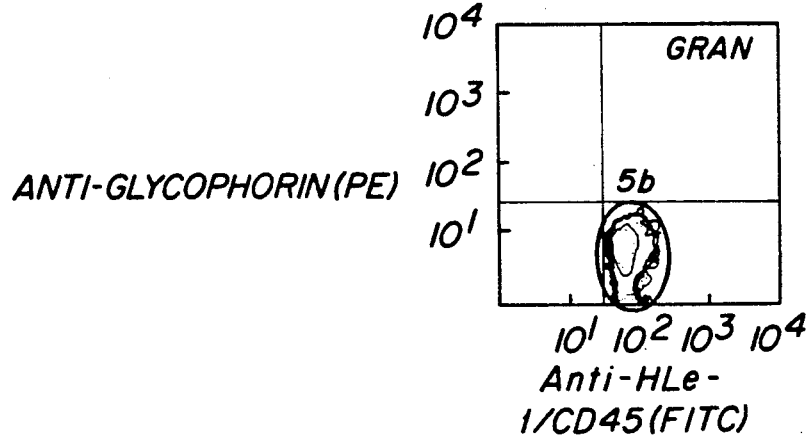
Figure 3G:
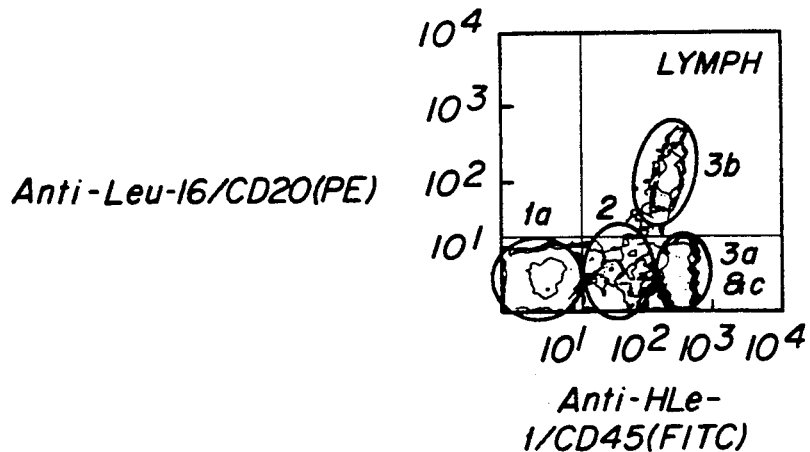
Figure 3H:
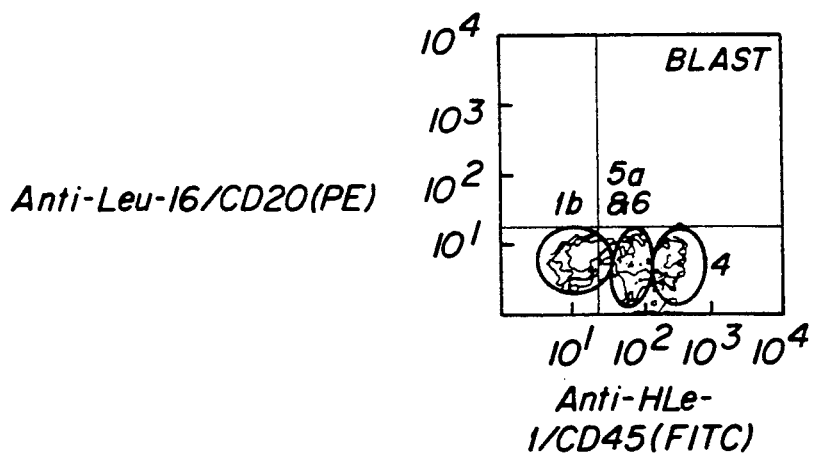
Figure 3I:
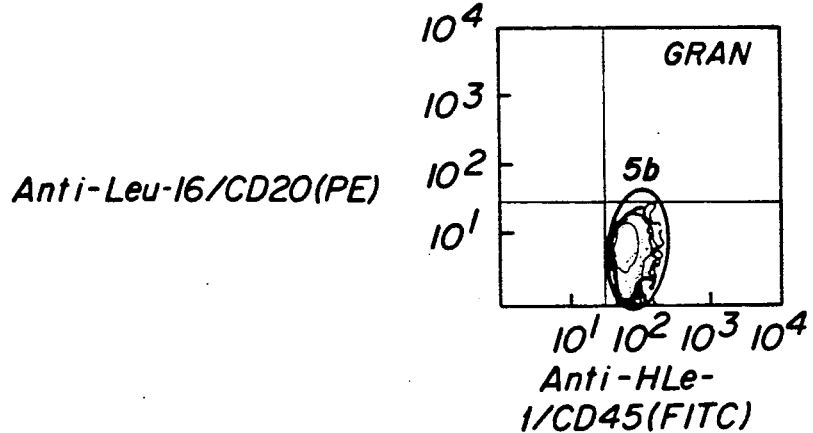

To detect T lymphocytes, normal bone marrow cells were reacted with Anti-Leu-4(PE), a CD3 pan T lymphocyte monoclonal antibody, and Anti-HLe-1(FITC). See FIG. 3B. All CD3+ T lymphoid cells (population 3a) were found in "LYMPH" light scattering window, with intense co-expression of CD45.

To detect B lymphocytes, bone marrow cells were reacted with Anti-Leu-12(PE) (CD19) in combination with Anti-HLe-1(FITC) to identify all B lymphoid cells, including both immature (population 2) and mature developmental stages (population 3b). The correlation between these two antigens is shown in FIG. 3D. All CD19+ B lymphoid cells were confined to "LYMPH" window. These B lineage cells had three distinct levels of CD45 expression: CD19+/CD45+++ (population 3b), CD19+/CD45++, and CD19+/CD45+ (population 2). In order to further discriminate maturational differences among B lineage cells, bone marrow cells were stained with CD45 in combination with two other monoclonal antibodies: Anti-CALLA(PE), (CD10) an antibody which identifies immature B lymphoid cells (not shown) or Anti-Leu-16(PE), (CD20), which identifies late B cells. Immature B cells expressing CD10 and intermediate levels of CD45 were identified in population 2.

Figure 4A:
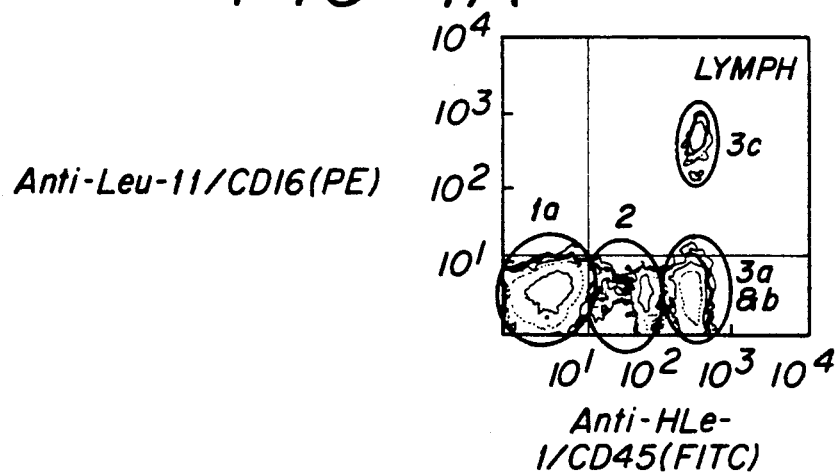
Figure 4B:
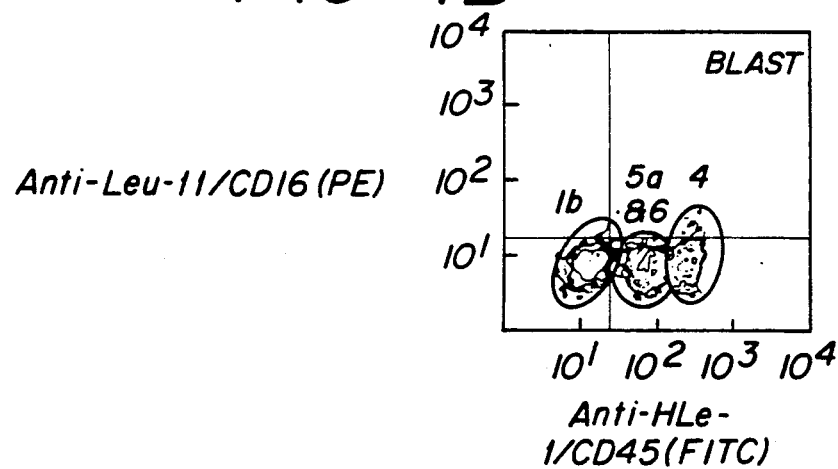
Figure 4C:
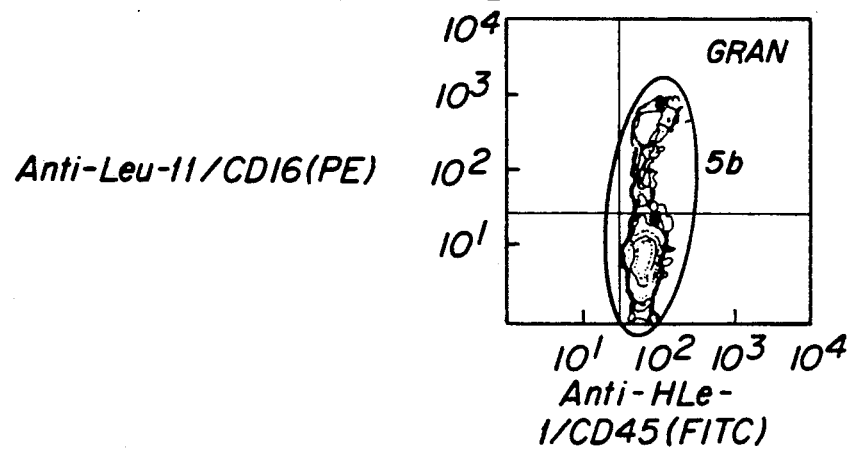

To detect NK cells, bone marrow cells were stained with Anti-HLe-1(FITC) in combination with either Anti-Leu-11(PE) (CD16) or Anti-Leu-15(PE) (CD11b). These monoclonal antibodies identify NK cells (population 3c) within the "LYMPH" light scattering window. The cells identified by these antibodies within the "LYMPH" light scattering window were bright for CD45+++. (FIGS. 4A and 4B.) The cells in the "BLAST" and "GRAN" windows which were labeled with CD16 and CD11b were monomyeloid cells, and are discussed below.

Cells of the monocytic lineage were identified by staining bone marrow cells with either CD11b or Anti-Leu-M3(PE) (CD14), monoclonal antibodies that bind to mature and maturing monocytes (population 4). The correlated expression of these two markers with CD45 are shown in FIGS. 4B and 5A.

Cells of the monocytic lineage were found only in the "BLAST" light scattering window and therefore could be distinguished from cells belonging to other lineages.

Figure 5A:
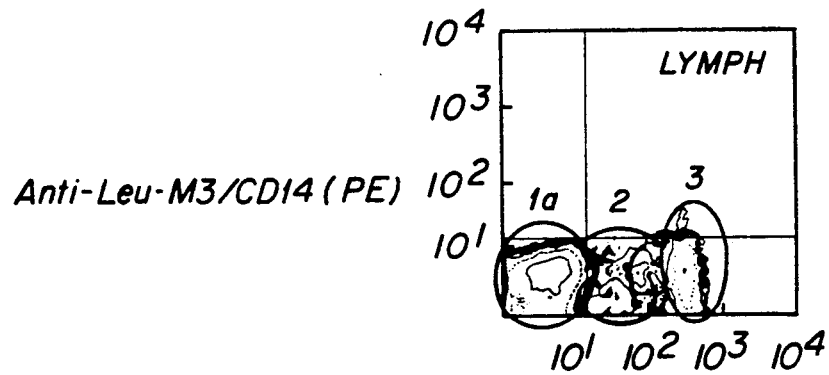

There were no CD14+ cells in the "LYMPH" window, while a small percentage of cells in the "GRAN" window were CD14+ (FIG. 5A).

The expression of CD11b antigens on the monocyte lineage could also be identified within the "BLAST" light scattering window. The convex shape of the bivariate plot (FIG. 4B, "BLAST") suggests that the expression of CD11b precedes the change in intensity of CD45 on the maturing monocytes (population 4). The highly correlated expression of CD14 and CD45 indicates that the change in intensity of CD45 during monocytic maturation coincides with the expression of CD14. Other studies have shown that CD11b precedes CD14 expression during monocyte development. The cells expressing CD11b found in the "LYMPH" window, FIG. 4B, were shown above to be NK cells (population 3c).

Development of myeloid cells was assessed by staining bone marrow cells with several monoclonal antibodies including CD15, CD11b, CD16 in combination with CD45. CD15 is intensely expressed on granulocytes (population 5a & b) and dimly expressed on monocytes (population 4) (FIG. 2). All maturing granulocytes with the "GRAN" window (population 5b) were intensely positive for CD15 and were intermediately positive for CD45. Within the "BLAST" gate, the more immature myeloid cells (myelocytes, promyelocytes) were brightly positive for CD15 and could be distinguished from the monocytes which were less positive for CD 15 but had higher levels of CD45 (population 4) (FIG. 2).

CD11b is expressed later during myeloid development than CD15. Only a portion of the "GRAN" cells (population 5b) expressed CD11b but all expressed CD15. Even fewer cells within the "GRAN" window reacted with CD16 (FIG. 4A). The cells within the "BLAST" window which reacted with CD11b (population 4) (FIG. 4B) were predominantly monocytes since they expressed slightly higher levels of CD45.

Figure 5B:
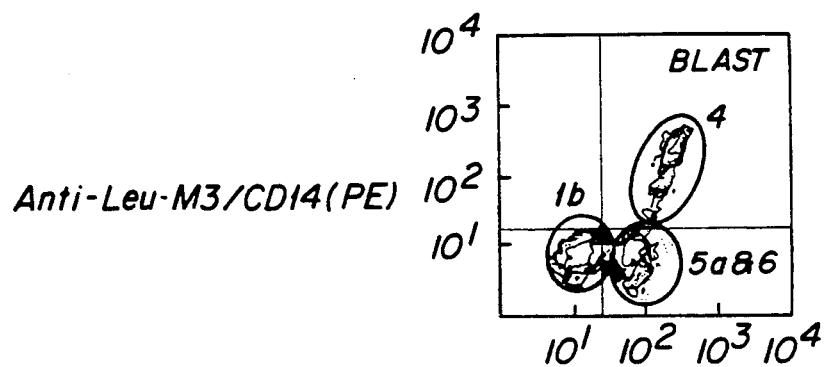
Figure 5C:
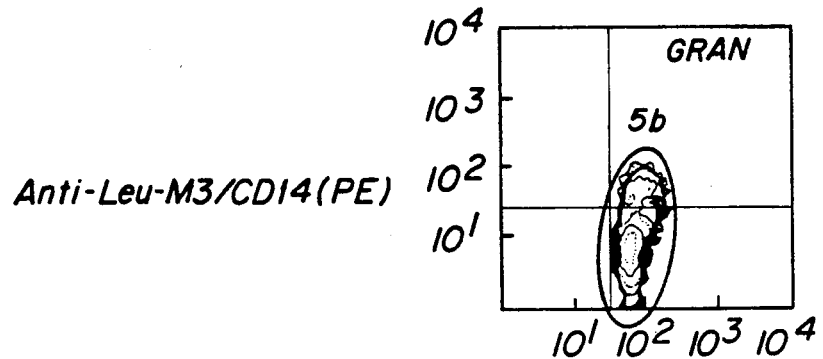
Figure 5D:
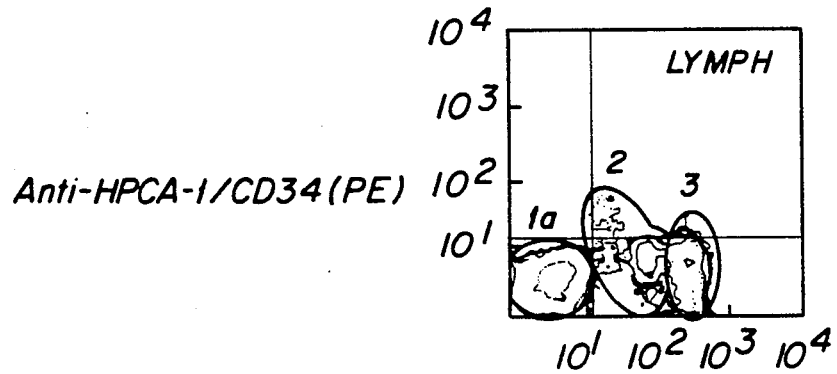
Figure 5E:
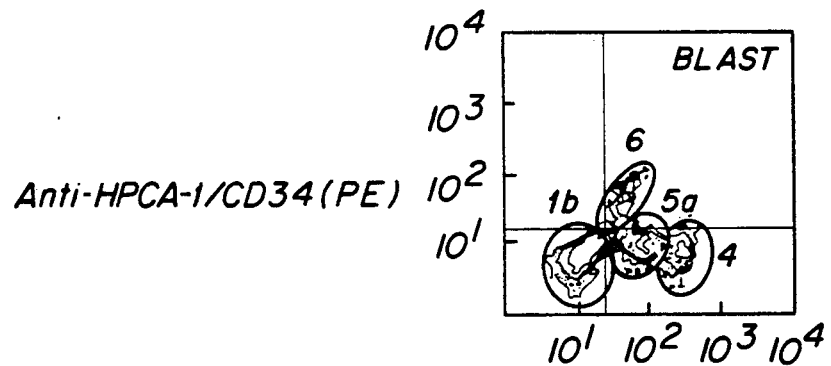
Figure 5F:
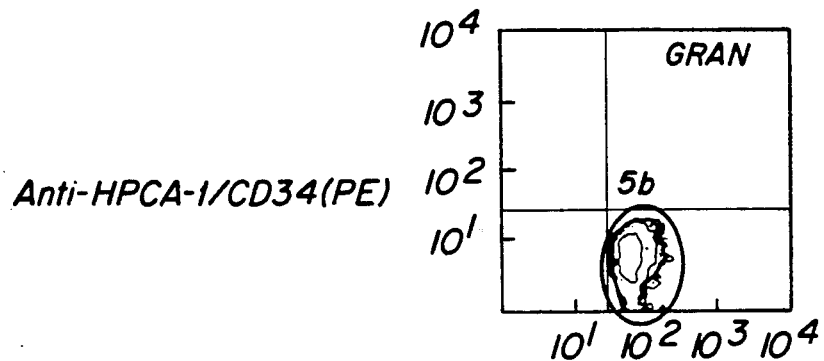

All cells capable of forming hematopoietic colonies express the human progenitor cell antigen, CD34[30]. The correlated expression of CD34 and CD45 on progenitor cells is shown in FIG. 5B. The CD34+ cells (population 6) were dimly positive for CD45. From previous studies it has been shown that approximately half of the CD34[30] positive cells are B lymphoid cells (population 2). These CD34+ immature B lymphoid cells were found in the "LYMPH" window and expressed CD19 and CD10. These cells were the same ones which were identified and discussed above, with the CD19 and CD10 B lineage markers shown in FIG. 3D. However, the remainder of CD34+ cells including myeloid and erythroid progenitors (population 6) which form colonies in in vitro assays were present in "BLAST" window (FIG. 5B) also expressing a low level of CD45.

In summary, the erythroid cells within the "LYMPH" light scattering window were easily distinguished from other cells within this window by their expression of GPA. The GPA+ erythroid cells, ranging from intermediate normoblast to the reticulocyte stage (population 1a), expressed little or no CD45. In contrast, the mature lymphocytes within this light scattering window, including CD3+ T cells (population 3a), CD16+ and CD11b+ NK cells (population 3c) and CD20+ mature B cells (population 3b) all expressed large amounts of the CD45 antigen.

The only other cells in this light scattering window were immature B lymphocytes (population 2), which expressed lesser amounts of CD45 than their mature descendants.

All of the cells within the "LYMPH" light scattering gate can be accounted for using these monoclonal antibodies. This window includes mature T (population 3a), B (population 3b) and NK (population 3c) lymphocytes as well as maturing erythroid (population 1a) and B lymphoid (population 2) cells which can be distinguished based on the amounts of CD45 expressed on their cell surfaces. No cells of the myeloid lineages appear within this light scattering window.

Three populations of cells within the "BLAST" light scattering window were distinguished based on the intensity of CD45 and CD15 antigen expression. The cells with the lowest CD45 antigen expression (CD45±) were erythroid (population 1b), as identified by their expresion of GPA. (FIG. 2B). The cells in this window which expressed the highest amount of CD45 were monocytic (population 4), as evidenced by the co-expression of the monocytic-specific CD14 antigen. These brighter CD45+ cells also expressed high levels of CD11b and intermediate amounts of CD15 antigens. The cells in the "BLAST" window which expressed intermediate amounts of CD45 were further subdividied by their expression of other cell surface antigens. CD15 divided these intermediate CD45+ cells into two populations. The bright CD15+ cells were committed to the neutrophil lineage (population 5a), including promyelocytes and myelocytes. The remaining CD15−, CD45+ cells include the CD34+; cells since CD15 and CD34 do not overlap in marrow. Thus, the progenitor cells (population 6), as identified in a positive manner by CD34+, were also be detected by the combination of CD45 and CD15.

All of the cells within the "GRAN" window were characterized as having granules in their cytoplasm and having low levels of CD45. CD15 labeled all of these cells, while CD11b or CD16 identified many fewer cells. CD14 identified minor populations of these "GRAN" window cells. These cells constituted different maturational stages of the neutrophil lineage (population 5b) with corresponding differences in myeloid antigen expression.

The in vitro assayed progenitor cells (population 6) and presumably the pluripotent stem cells are found in the "BLAST" light scattering window. These cells express low levels of CD45 on their surfaces. As cells are committed to the erythroid lineage, their CD45 expression decreases as they begin expressing erythroid antigens such as GPA. CD45 expression decreases progressively with further maturation of these cells accompanied by a decrease in forward light scattering.

As progenitor cells (population 6) become committed to the B lineage (population 2) they maintain CD34 expression and begin expressing CD10 and CD19. This is accompanied by a decrease in their forward light scattering cell size while they maintain a low level of expression of CD45. As the B lineage cells continue to mature, they lose CD34 and increase expression of CD45. The final stages of B lymphoid maturation (population 3b) are characterized by a further increase in CD45 expression, acquisition of CD20, and loss of CD10.

Once cells become committed to the monocyte lineage (4), they begin to express CD11b, followed by an increase in CD45 levels accompanied by the acquisition of CD14. The maturing monocytes also express CD15 but in lower amounts than granulocytes.

The commitment of progenitor cells (population 6) to the granulocytic maturation (population 5b) does not cause a change in CD15 expression. Although several other antigens become expressed on this lineage during the maturation process, the level of CD45 expression remains low and constant.

These and other embodiments of the invention may suggest themselves to those skilled in the art. Accordingly, this disclosure should not be taken in a limiting sense.

What is claimed:

1. A method for the simultaneous detection of different lineages and maturational stages of bone marrow cells in a sample comprising the steps of isolating the sample from an individual, reaction the sample with a first monoclonal antibody and a second monoclonal antibody to form a mixture, wherein said first monoclonal antibody is selected so as to react differentially with substantially all leukocytes and the second monoclonal antibody is selected so as to react differentially with a subpopulation of leukocytes and wherein said first and second monoclonal antibodies are conjugated with different fluorochromes having distinct emission spectra, and analyzing the mixture by means capable of measuring cell size, granularity and fluorescence of the cells in the sample, wherein cell size, granularity and relative fluorescence intensity are used to distinguish between lineages and between maturational stages in each of the lineages.

2. The method according to claim 1 wherein the first monoclonal antibody is anti-CD45.

3. The method according to claim 1 wherein the first monoclonal antibody is conjugated to fluoroscein isothiocyanate.

4. The method according to claim 1 wherein the second monoclonal antibody is selected from the group consisting of anti-CD15, anti-CD16, anti-CD10, anti-CD34, anti-CD20, anti-CD19, anti-CD14, anti-CD3 and anti-CD 11b.

5. The method according to claim 4 wherein the second monoclonal antibody is anti-CD15.

6. The method according to claim 1 wherein the second monoclonal antibody is conjugated to pycoerythrin.

7. The method according to claim 1 wherein said means comprise a flow cytometer.

8. A method for the detection and analysis of different lineages and maturational stages of bone marrow cells in a sample comprising the following steps of isolating the sample from an individual, reacting the sample with an anti-CD45 monoclonal antibody and an anti-CD15 monoclonal antibody to form a mixture, wherein said antibodies are conjugated with different fluorochromes having distinct emission spectra, and analyzing the mixture by flow cytometry means to distinguish between different lineages and maturational stages of cells in the sample based upon cell size, granularity and relative fluroescence emission wherein cell size and granularity are used first to distinguish between the lymphocytes, blasts and granulocytes and relative fluorescence emission then is used to distinguish between maturational stages in each of the lineages when a gate is sequentially set for each lineage.

9. The method according to claim 8 wherein the step of isolating the sample further comprises isolating the leukocytes in the sample.

10. The method according to claim 8 wherein the anti-CD15 and anti-CD45 monoclonal antibodies are labeled with fluorescein isothiocyanate and phycoerythrin respectively.

11. A kit for the detection and identification of different lineages and stages of hematopoietic cells in a sample comprising a first monoclonal antibody and second monoclonal antibody, wherein said first monoclonal antibody reacts differentially with essentially all leukocytes and said second monclonal antibody reacts differentially with a subpopulation of leukocytes and wherein said first and second monoclonal antibodies are conjugated with different fluorochromes having distinct emission spectra.

12. The kit according to claim 11 wherein the first monoclonal antibody is anti-CD45.

13. The kit according to claim 11 wherein the second monoclonal antibody is anti-CD15.

14. The kit according to claim 11 wherein the first and second monoclonal antibodies are labeled with fluorescein isothiocyanate and phycoerythrin respectively.

* * * * *